United States Patent
Sieloff

Patent Number: 5,759,689
Date of Patent: Jun. 2, 1998

[54] COEXTRUDED POLYCARBONATE SHEET WITH IMPROVED WEATHERING

[75] Inventor: Ronald F. Sieloff, Evansville, Ind.

[73] Assignee: General Electric Company, Pittsfield, Mass.

[21] Appl. No.: 664,034

[22] Filed: Jun. 13, 1996

[51] Int. Cl.$^6$ .......................... B32B 27/36; C08G 63/48; C08F 20/00
[52] U.S. Cl. .......................... 428/412; 525/67; 525/439; 525/462; 525/469; 568/313
[58] Field of Search .................. 428/412; 525/67, 525/439, 462, 469; 568/313

[56] References Cited

U.S. PATENT DOCUMENTS

| | | |
|---|---|---|
| 2,999,835 | 9/1961 | Goldberg. |
| 3,027,814 | 4/1962 | Schnelman. |
| 3,028,365 | 4/1962 | Schnell. |
| 3,030,331 | 4/1962 | Goldberg. |
| 3,153,008 | 10/1964 | Fox. |
| 3,169,121 | 2/1965 | Goldberg. |
| 3,275,601 | 9/1966 | Schnell. |
| 3,334,154 | 8/1967 | Kim. |
| 3,635,895 | 1/1972 | Kramer. |
| 3,915,926 | 10/1975 | Wambach. |
| 4,188,314 | 2/1980 | Fox. |
| 4,198,465 | 4/1980 | Moore et al.. |
| 4,455,205 | 6/1984 | Olson. |
| 4,477,529 | 10/1984 | Campbell. |
| 4,478,876 | 10/1984 | Chung. |
| 4,486,504 | 12/1984 | Chung. |
| 4,487,896 | 12/1984 | Mark. |
| 5,061,558 | 10/1991 | Fischer et al. ............... 428/332 |
| 5,108,835 | 4/1992 | Hahnsen et al. ............... 428/334 |

FOREIGN PATENT DOCUMENTS

| | | |
|---|---|---|
| 0 247 480 A2 | 12/1987 | European Pat. Off.. |
| 0 672 732 A1 | 9/1995 | European Pat. Off.. |
| 0 704 437 A2 | 4/1996 | European Pat. Off.. |
| 0 709 442 A2 | 5/1996 | European Pat. Off.. |
| 786 144 | 11/1957 | United Kingdom. |

*Primary Examiner*—Mark Chapman

[57] ABSTRACT

A compound of the formula:

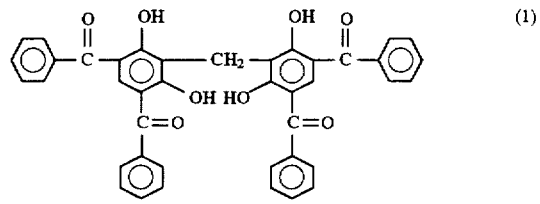

is blended with a polycarbonate resin to obtain an ultraviolet light degradation resistant article.

8 Claims, No Drawings

COEXTRUDED POLYCARBONATE SHEET WITH IMPROVED WEATHERING

BACKGROUND OF THE INVENTION

1. Field of the Invention

The invention relates to weather resistant polycarbonate resin articles and more particularly a polycarbonate resin blend containing an ultra-violet radiation resistance enhancer.

2. Brief Description of the Related Art

Polycarbonate resins have been useful thermoplastic molding resins, to mold particular articles of certain physical properties, including film.

Coating polymeric resin substrates such as articles of molded polycarbonate and the like to improve their resistance to weathering is an accepted procedure. Advantageously, the coatings are comprised of radiation curable polyacrylic or polyacrylic-urethane coatings; see for example the coating descriptions set forth in the U.S. Pat. Nos. 4,198,465; 4,455,205; 4,477,529; 4,478,876; and 4,486,504.

SUMMARY OF THE INVENTION

The invention comprises a thermoplastic polycarbonate resin blend, which comprises:

a thermoplastic, aromatic polycarbonate resin; and an ultra-violet light absorbing proportion of a dimer having the structural formula:

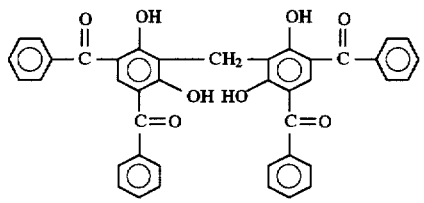

(1)

The resin blend is useful to prepare weather resistant sheets and films, particularly useful to cap or laminate over the surface of molded polycarbonate articles.

The invention also comprises articles extruded from the compositions of the invention, which advantageously exhibit improved weathering without significant loss of properties.

The compositions of the invention are useful to thermoplastically mold articles such as structural panels and the like, which are useful in the fabrication of housings, interior furnishings and the like.

DETAILED DESCRIPTION OF THE PREFERRED EMBODIMENTS OF THE INVENTION

Thermoplastic, aromatic polycarbonate resins and their method of preparation by interfacial polymerization are well known; see for example the details provided in the U.S. Pat. Nos. 3,028,365; 3,334,154; 3,275,601; 3,915,926; 3,030,331; 3,169,121; 3,027,814; and 4,188,314, all of which are incorporated herein by reference thereto.

Included within the meaning of the term "polycarbonate" as used herein are the polyester-carbonates prepared by interfacial polymerization technique, well known to those skilled in the art; see for example the U.S. Pat. Nos. 3,169,121 and 4,487,896 which are incorporated herein by reference thereto.

In general, the method of interfacial polymerization comprises the reaction of a dihydric phenol with a carbonyl halide (the carbonate precursor). The polyester-carbonates are prepared in the further presence of a dicarboxylic acid (ester precursor).

Although the reaction conditions of the preparative processes may vary, several of the preferred processes typically involve dissolving or dispersing the diphenol reactants in aqueous caustic, adding the resulting mixture to a suitable water immiscible solvent medium and contacting the reactants with the carbonate and ester precursors, under controlled pH conditions. The most commonly used water immiscible solvents include methylene chloride, 1,2-dichloroethane, chlorobenzene, toluene, and the like.

Advantageously a catalyst is added to the reaction mixture to promote the reaction. The catalyst employed accelerates the rate of polymerization of the dihydric phenol reactant with the carbonate precursor. Representative catalysts include but are not limited to tertiary amines such as triethylamine, quaternary phosphonium compounds, quaternary ammonium compounds, and the like.

The preferred process for preparing polycarbonate resins comprises a phosgenation reaction. The temperature at which the phosgenation reaction proceeds may vary from below 0° C., to above 100° C. The phosgenation reaction preferably proceeds at temperatures of from about room temperatures (25° C.) to 50° C. Since the reaction is exothermic, the rate of phosgene addition may be used to control the reaction temperature. The amount of phosgene required will generally depend upon the amount of the dihydric phenol reactant added.

The dihydric phenols employed are known, and the reactive groups are the two phenolic hydroxyl groups. Some of the dihydric phenols are represented by the general formula:

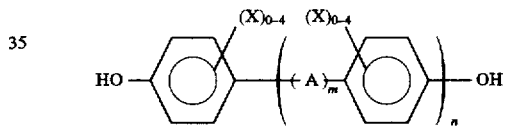

wherein A is a divalent hydrocarbon radical containing from 1 to about 15 carbon atoms; a substituted divalent hydrocarbon radical containing from 1 to about 15 carbon atoms and substituent groups such as halogen; —S—; —S(O)—; —S(O)$_2$—; —O—; or —C(O)—; each X is independently selected from the group consisting of hydrogen, halogen, and a monovalent hydrocarbon radical such as an alkyl group of from 1 to about 8 carbon atoms, an aryl group of from 6–18 carbon atoms, an aralkyl group of from 7 to about 14 carbon atoms, an alkaryl group of from 7 to about 14 carbon atoms, an alkoxy group of from 1 to about 8 carbon atoms, or an aryloxy group of from 6 to 18 carbon atoms; and m is zero or 1 and n is an integer of from 0 to 5.

Typical of some of the dihydric phenols employed are bis-phenols such as (4-hydroxyphenyl)methane, 2,2-bis(4-hydroxyphenyl)propane (also known as bisphenol-A), 2,2-bis(4-hydroxy-3,5-dibromophenyl)propane; dihydric phenol ethers such as bis(4-hydroxyphenyl) ether, bis(3,5-dichloro-4-hydroxyphenyl) ether; dihydroxydiphenyls such as p,p'-dihydroxydiphenyl, 3,3'-dichloro-4,4'-dihydroxydiphenyl; dihydroxyaryl sulfones such as bis(4-hydroxyphenyl) sulfone, bis (3,5-dimethyl-4-hydroxyphenyl) sulfone, dihydroxybenzenes such as resorcinol, hydroquinone, halo- and alkyl-substituted dihydroxybenzenes such as 1,4-dihydroxy-2,5-dichlorobenzene, 1,4-dihydroxy-3-methylbenzene; and dihydroxydiphenyl sulfides and sulfoxides such as bis(4-hydroxyphenyl) sulfide, bis(4-hydroxyphenyl) sulfoxide and bis(3,5-dibromo-4-hydroxyphenyl) sulfoxide. A variety of additional dihydric phenols are available and are disclosed in U.S. Pat. Nos. 2,999,835; 3,028,365 and 3,153,008; all of which are incorporated herein by reference thereto. It is, of course, possible to employ two or more different dihydric phenols or a combination of a dihydric phenol with a glycol.

The carbonate precursor can be either a carbonyl halide, a diarylcarbonate or a bishaloformate. The carbonyl halides include carbonyl bromide, carbonyl chloride, and mixtures thereof. The bishaloformates include the bishaloformates of dihydric phenols such as bischloroformates of 2,2-bis(4-hydroxyphenyl)-propane, 2,2-bis(4-hydroxy-3,5-dichlorophenyl)-propane, hydroquinone, and the like, or bishaloformates of glycols such as bishaloformates of ethylene glycol, and the like. While all of the above carbonate precursors are useful, carbonyl chloride, also known as phosgene, is preferred.

In general, any dicarboxylic acid conventionally used in the preparation of linear polyesters may be utilized as the ester precursor in the preparation of the polyester-carbonate resins. Generally, the dicarboxylic acids which may be utilized include the aliphatic dicarboxylic acids, the aromatic dicarboxylic acids, and the aliphatic-aromatic dicarboxylic acids. These acids are well known and are disclosed for example in U.S. Pat. No. 3,169,121 which is hereby incorporated herein by reference. Representative of dicarboxylic acids are those represented by the general formula:

HOOC—R¹—COOH wherein R¹ represents a divalent aliphatic radical such as alkylene, alkylidene, cycloalkylene or substituted alkylene or alkylidene; an aromatic radical such as phenylene, naphthylene, biphenylene, substituted phenylene and the like; a divalent aliphatic-aromatic hydrocarbon radical such as an aralkyl or alkaryl radical; or two or more aromatic groups connected through non-aromatic linkages of the formula:

—E— wherein E is a divalent alkylene or alkylidene group. E may also consist of two or more alkylene or alkylidene groups, connected by a non-alkylene or alkylidene group, connected by a non-alkylene or non-alkylidene group, such as an aromatic linkage, a tertiary amino linkage, an ether linkage, a carbonyl linkage, a silicon-containing linkage, or by a sulfur-containing linkage such as sulfide, sulfoxide, sulfone and the like. In addition, E may be a cycloaliphatic group of five to seven carbon atoms, inclusive, (e.g. cyclopentyl, cyclohexyl), or a cycloalkylidene of five to seven carbon atoms, inclusive, such as cyclohexylidene. E may also be a carbon-free sulfur-containing linkage, such as sulfide, sulfoxide or sulfone; an ether linkage; a carbonyl group; a direct bond; a tertiary nitrogen group; or a silicon-containing linkage such as silane or siloxy. Other groups which E may represent will occur to those skilled in the art.

Some non-limiting examples of aromatic dicarboxylic acids which may be used in preparing the poly(ester-carbonate) include phthalic acid, isophthalic acid, terephthalic acid, homophthalic acid, o-, m-, and p-phenylenediacetic acid, and the polynuclear aromatic acids such as diphenyl dicarboxylic acid, and isomeric naphthalene dicarboxylic acids. The aromatics may be substituted with Y groups. Y may be an inorganic atom such as chlorine, bromine, fluorine and the like; an organic group such as the nitro group; an organic group such as alkyl; or an oxy group such as alkoxy, it being only necessary that Y be inert to and unaffected by the reactants and the reaction conditions. Particularly useful aromatic dicarboxylic acids are those represented by the general formula:

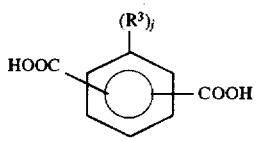

wherein j is a positive whole integer having a value of from 0 to 4 inclusive; and each $R^3$ is independently selected from the group consisting of alkyl radicals, preferably lower alkyl (1 to about 4 carbon atoms).

Most preferred as aromatic dicarboxylic acids are isophthalic acid, terephthalic acid, and mixtures thereof.

Representative of aliphatic dicarboxylic acids within the formula given above wherein $R^1$ is alkylene are butanedioic acid, hexanedioic acid, octanedioic acid, decanedioic acid, dodecanedioic acid and the like. Preferred are dicarboxylic acids having from 4 to 18 carbon atoms, inclusive. $R^1$ is an alkylene radical such as ethylene, nonylene, decylene, or substituted alkylene. Mixtures of the dicarboxylic acids may be employed. Therefore, where the term dicarboxylic acid is used herein it is to be understood that this term includes mixtures of two or more dicarboxylic acids.

The proportions of reactants employed to prepare the polyester-carbonate resins will vary in accordance with the proposed use of the product composition. Those skilled in the art are aware of useful proportions, as described in the U.S. patents referred to above. In general, the amount of the ester bonds may be from about 5 to about 90 mole percent, relative to the carbonate bonds. For example, 5 moles of bisphenol A reacting completely with 4 moles of isophthaloyl dichloride and 1 mole of phosgene would give a polyester-carbonate of 80 mole percent ester bonds.

The preferred polycarbonates for use in the present invention are those derived from bisphenol A and phosgene and having an intrinsic viscosity of about 0.3 to about 1.5 deciliters per gram in methylene chloride at 25° C.

In the conventional interfacial polymerization methods of preparing polycarbonates a molecular weight regulator (a chain stopper) is generally added to the reaction mixture prior to or during the contacting with carbonate and ester precursors. Useful molecular weight regulators include, but are not limited to, monohydric phenols such as phenol, chroman-I, paratertiarybutylphenol, p-cumylphenol and the like. Techniques for the control of molecular weight are well known in the art and are used for controlling the molecular weight of the polycarbonate resins used in the present invention.

Included within the term "polycarbonates" as used herein are high molecular weight thermoplastic randomly branched polycarbonates. These randomly branched polymers are prepared by co-reacting a polyfunctional organic compound with a dihydric phenol, carbonate and/or ester precursors. The polyfunctional organic compounds useful in making the branched polycarbonates are set forth in U.S. Pat. Nos. 3,635,895 and 4,001,184 which are incorporated herein by reference. These polyfunctional compounds are generally aromatic and contain at least three functional groups which are carboxyl, carboxylic anhydrides, phenols, haloformyls or mixtures thereof. Some nonlimiting examples of these polyfunctional aromatic compounds include 1,1,1-tri(4-hydroxyphenyl) ethane, 1,3,5-trihydroxybenzene, trimellitic anhydride, trimellitic acid, trimellityl trichloride, 4-chloroformyl phthalic anhydride, pyromellitic acid, pyromellitic dianhydride, mellitic acid, mellitic anhydride, trimesic acid, benzophenonetetracarboxylic acid, benzophenonetetracarboxylic dianhydride, and the like. The preferred polyfunctional aromatic compounds are 1,1,1-tri (4-hydroxyphenyl) ethane, trimellitic, anhydride or trimellitic acid or their haloformyl derivatives. Also included herein are blends of a linear polycarbonate and a branched polycarbonate.

Those skilled in the art will appreciate that preferred polycarbonates described herein may be characterized as containing recurring polycarbonate chain units of the formula:

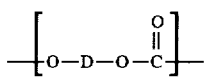

wherein D is a divalent aromatic radical of the dihydric phenol employed in the resin preparation; and may also include repeating or recurring carboxylic chain units of the formula:

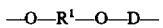

wherein D and $R^1$ have the meanings previously ascribed to them.

The ultra-violet light absorbing compound of formula (I) given above is bis(2,6-dihydroxy-3,5-dibenzoylphenyl) methane, which may be referred to herein for convenience as "DBRA". An ultra-light absorbing proportion is one generally within the range of from 3 to 15 parts by weight of the polycarbonate resin.

Articles formed from the blend of the invention may also contain fibrous reinforcing agents. Fibrous reinforcing agents employed in plastic molding compositions are generally well known and are represented by glass fibers, mineral fibers such as rockwool, carbon fibers and the like. Preferred reinforcing agents are glass fibers such as cut glass filaments (long glass fiber and short glass fiber) rovings and staple fiber.

The filamentous glass that may be used in the embodiments of this invention are well known to those skilled in the art and is widely available from a number of manufacturers. The glass may be untreated or, preferably, treated with silane or titanate coupling agents.

The length of the glass filaments and whether or not they are bundled into fibers and the fibers bundled in turn to yarns, ropes or rovings, or woven into mats, and the like, are also not critical to the invention. However, in preparing the molding compositions, it is convenient to use the filamentous glass in the form of chopped strands of from about 0.25 cm to about 5 cm long. In articles molded from the compositions, on the other hand, even shorter lengths will be encountered because, during compounding, considerable fragmentation will occur. This is desirable, however, because the best properties are exhibited by thermoplastic injection molded articles in which the filament lengths lie between about 0.0005 to 0.05 cm.

The blends of the invention may include an impact-modifying proportion of an impact modifier. Any of the known impact modifiers for polycarbonates may be used. Representative of such impact-modifiers are selectively hydrogenated linear, sequential or radial teleblock copolymers of a vinyl aromatic compound (A) and (A')$_n$ and an olefinic elastomer (B) of the A—B—A'; A (B—A—B)$_n$A; A (B—A)$_n$B; or B [(A—B$_n$) B]$_4$ type wherein n is an integer of from 1 to 10 inclusive, see for example Haefele et al, U.S. Pat. No. 3,333,024, which is incorporated herein by reference.

Preferred as an impact-modifier used in the compositions of the invention are the so-called "ABS" polymers. ABS polymers are defined, for example, in the Modern Plastics Encyclopedia, 1989 edition, page 92, as the family of thermoplastics made from the three monomers acrylonitrile, butadiene and styrene, and more specifically as a mixture (alloy) of styrene-acrylonitrile copolymer with SAN-grafted polybutadiene rubber.

Impact-modifying agents for use with the polyester-carbonate based compositions of the invention also include the various polyacrylate resins known in the art. For example, polyacrylates are commercially available from many sources, e.g., Rohm & Haas Chemical Company, Philadelphia, Pa. under the trade designations Acryloid® KM 330, and 7709 XP; Goodyear Tire & Rubber Company, Akron, Ohio under the trade designation RXL® 6886; from American Cyanamid Company, Stamford, Conn., under the trade designation Cyanacryl® 770; from M&T Chemicals Co., Trenton, N.J., under the trade designation Durostrength® 200; and from Polysar Corporation, Canada, under the trade designation Polysar® §1006. In general any of the polyalkyl acrylates described by Brinkman et al., U.S. Pat. No. 3,591,659, incorporated herein by reference thereto, can be used, especially those containing units derived from n-butyl acrylate.

The polyacrylate resin impact modifiers may be added to the compositions of the invention in conventional amounts of from 0.01% to 50% by weight based on the weight of the overall composition and usually in amounts of from 0.01% to 10% by weight on the same basis.

Another class of known impact modifiers which may be used as an ingredient of the resin blend of the invention are polyamide-polyether block copolymers which may be represented by the formula:

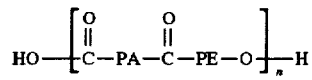

wherein PA represents the polyamide segment, PE represents a polyether segment and n is an integer such that the block copolymer has a weight average molecular weight ($M_w$) of from about 5,000 to about 100,000. Polyamide-polyether block copolymers of the class described above are generally well known and may be prepared for example by the condensation reaction of a prepolyamide and a polyoxyalkylene glycol, by conventional technique; see for example the preparative methods described in U.S. Pat. Nos. 4,208, 493; 4,230,838; 4,361,680; and 4,331,786, all of which are incorporated herein by reference thereto. The polyamide-polyether block copolymers so prepared are commercially available and may be wide ranging in their make-up from a wide range of prepolyamides and polyoxyalkylene glycols.

Impact-modifying proportions of the polyamide-polyether block copolymers are generally within the range of from about 0.1 to 10 percent by weight of the resin composition.

Preferred embodiment compositions of the invention include as an additive ingredient flame retarding agents. In general, the presence of impact-modifiers in polycarbonate based molding compositions is degradative to the action of fire retardants. However, in the compositions of the present invention, reductions in flame-retardance due to presence of the impact-modifier is unexpectedly not significant.

Some particularly useful flame retardants are the alkali and alkaline earth metal salts of sulfonic acids. These types of flame retardants are disclosed in U.S. Pat. Nos. 3,933,734;

3,931,100; 3,978,024; 3,948,851; 3,926,980; 3,919,167; 3,909,490; 3,953,396; 3,953,300; 3,917,559; 3,951,910 and 3,940,366, all of which are hereby incorporated herein by reference.

Preferred as a flame retarding additive for use in the compositions of the invention are the halogenated polycarbonate resins such as tetrabromobisphenol polycarbonate.

The tetrabromobisphenol polycarbonate can be any of the homopolycarbonates made from tetrabromobisphenol A and phosgene or the copolycarbonates made using partly tetrabromobisphenol A and partly bisphenol A. The homopolycarbonates are available for example from Great Lakes Chemical Corp. as BC-52 and BC-58; BC-52 is an oligomer of tetrabromobisphenol A polycarbonate with phenoxy end groups on the chain; BC-58 is similar but with 2,4,6-tribromophenoxy end groups on the chain. The copolymers of tetrabromobisphenol A and bisphenol A are described and their preparation given by Womback, U.S. Pat. No. 3,915,926, incorporated herein by reference thereto. The preferred tetrabromobisphenol A polycarbonate is one having about 50% tetrabromobisphenol A and 50% bisphenol A units on a molar basis.

Flame-retarding proportions of flame retardants vary in accordance with the specific flame retardant. In general, a flame-retarding proportion comprises from 0.01 to about 20 weight percent of the total composition.

The production of the compositions of the invention is done by any of the blending operations known for the blending of thermoplastics, for example blending in a kneading machine such as a Banbury mixer or an extruder. The sequence of addition is not critical but all components should be thoroughly blended together. Blending can be done continuously or batchwise. Melt blending can also be employed.

The thermoplastic compositions of the invention may also be compounded with conventional molding aids such as, for example, antioxidants; antistatic agents; and the like; hydrolytic stabilizers such as the epoxides disclosed in U.S. Pat. Nos. 3,489,716, 4,138,379 and 3,839,247, all of which are incorporated herein by reference; color stabilizers such as the organophosphites; thermal stabilizers such as phosphite; mold release agents and the like.

The following examples describe the manner and process of making and using the invention and set forth the best mode contemplated by the inventor for carrying out the invention but are not to be construed as limiting the scope of the invention. All parts are by weight unless otherwise stated.

Weatherability Test:

Using a Q.U.V. accelerated weathering tester manufactured by Q-Panel Company, each sample was exposed to ultraviolet rays from a 313B lamp for 2200 hours in total through cycles consisting of exposure at 60° C. under dry conditions for 8 hours and subsequent placing in a dark place under wet conditions at 60° C. for 4 hours. The Q.U.V. accelerated weathering test followed the "light and water exposure test for non-metallic materials" prescribed in ASTM G53-84.

Yellow Index (YI)

Measured on a Gardner Colorimeter model XL-835 after the accelerated aging test, prescribed in Test method ASTM D1925, after weathering.

Haze

Determined in accordance with Test Method ASTM D-1003, after weathering.

EXAMPLE 1

A film of polycarbonate resin is extruded from a blend of:

100 parts polycarbonate resin (Lexan® 130, General Electric Co., Pittsfield, Mass.

6.38 parts DBRA (formula I, supra.).

0.1 parts phosphite heat stabilizer in a two-shaft extruder (ZSK 32, Werner and Pfleider). Sheets of the film, 25 cm. in length by 5 cm in width and having a thickness of 5 mils were prepared and tested. The test results are given in the Table below.

EXAMPLES 2 AND 3

Examples 2 and 3 are not examples of the invention, but are made for purposes of comparison.

The procedure of Example, supra. is repeated except that in place of the DBRA an equal weight proportion of Tinuvin® 234* (Example 2) or Tinuvin® 400** (Example 3), Ciba-Geigy Corporation, Hawthorne, N.Y., is used. The test specimens of film, upon testing are as shown in the Table, below.

TABLE

| EXAMPLE | YELLOWNESS INDEX (AFTER WEATHERING) | HAZE (AFTER WEATHERING) |
|---|---|---|
| 1. DBRA PC blend | 2.9 | 2.0 |
| 2. T234 PC blend | 3.6 | 2.2 |
| 3. T400 PC blend | 3.2 | 2.2 |

The cured extruded blend of the invention (Example 1) exhibit improved resistance to weathering and is useful to enhance the weatherability of articles subject to weathering. Representative of advantageous articles of the invention are laminate housings for articles such as gasoline delivery pumps, marine articles, outdoor equipment, signage and the like.

* Tinuvin® 234 is a hydroxybenzotriazole of formula (I) described in U.S. Pat. No. 5,001,177.

** Tinuvin® 400 is a compound of the formula:

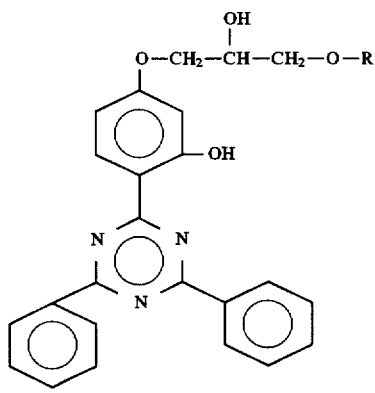

wherein R is a mixture of $C_{12}H_{25}$ and $C_{13}H_{27}$.

What is claimed is:

1. A thermoplastic polycarbonate resin blend, which comprises;

a thermoplastic, aromatic polycarbonate resin; and an ultra-violet light absorbing proportion of a dimer having the structural formula:

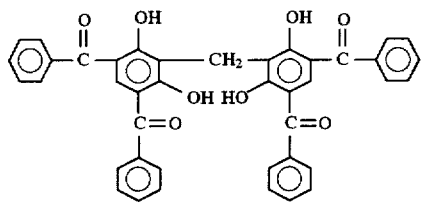

(1)

2. The blend of claim 1 which further comprises an impact-modifying proportion of an impact-modifier.

3. The blend of claim 1 wherein the polycarbonate resin has recurring carbonate chain units of the formula:

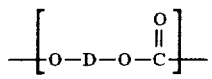

(I)

wherein D is a divalent aromatic radical of the formula:

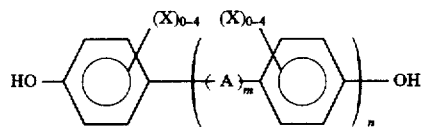

wherein A is a divalent hydrocarbon radical containing from 1 to about 15 carbon atoms; a substituted divalent hydrocarbon radical containing from 1 to about 15 carbon atoms and substituent groups such as halogen; —S—; —S(O)—; —S(O)$_2$—; —O—; or —C(O)—; each X is independently selected from the group consisting of hydrogen, halogen, and a monovalent hydrocarbon radical such as an alkyl group of from 1 to about 8 carbon atoms, an aryl group of from 6–18 carbon atoms, an aralkyl group of from 7 to about 14 carbon atoms, an alkaryl group of from 7 to about 14 carbon atoms, an alkoxy group of from 1 to about 8 carbon atoms, or an aryloxy group of from 6 to 18 carbon atoms; and m is zero or 1 and n is an integer of from 0 to 5; interrupted by recurring carboxylic chain units of the formula:

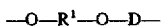

wherein D is as defined above and $R^1$ is a divalent alkylene, alkylidiene or cycloalkylene radical; a divalent aromatic radical; a divalent aliphatic-aromatic hydrocarbon radical; or two or more aromatic groups connected through non-aromatic linkages of the formula:

—E— wherein E is a divalent alkylene or alkylidene group; two or more alkylene or alkylidene groups, connected by a non-alkylene or alkylidene group, connected by a non-alkylene or non-alkylidene group; a cycloaliphatic group of five to seven carbon atoms, inclusive; a cycloalkylidene of five to seven carbon atoms, inclusive; carbon-free sulfur-containing linkage; a carbonyl group; a direct bond; a tertiary nitrogen group; or a silicon-containing linkage.

4. The composition of claim 1 wherein the polycarbonate is the phosgenation product of bisphenol-A and an aliphatic diacid of the formula:

HOOC—$R^1$—COOH wherein $R^1$ is alkylene.

5. The composition of claim 1 which further comprises a fibrous reinforcing agent.

6. An article thermoplastically molded from the composition of claim 1.

7. A weatherable, coextruded article, which comprises an unprotected base resin of a formed polycarbonate having a thickness of from 1 to 500 mils, having adhered thereto a 1 to 10 mil thick protective layer of the composition of claim 1.

8. The article of claim 7 wherein the base resin is a straight chain aromatic polycarbonate.

* * * * *